United States Patent [19]
Thigpen

[11] Patent Number: 5,616,736
[45] Date of Patent: Apr. 1, 1997

[54] METHOD OF PREPARING CYCLIC FORMALS

[75] Inventor: Hubert H. Thigpen, Corpus Christi, Tex.

[73] Assignee: Hoechst Celanese Corporation, Somerville, N.J.

[21] Appl. No.: 191,689

[22] Filed: Feb. 4, 1994

[51] Int. Cl.$^6$ .................. C07D 317/10; C07D 317/12
[52] U.S. Cl. ............................................ 549/430
[58] Field of Search ................................ 549/430

[56] References Cited

U.S. PATENT DOCUMENTS 3,857,759  12/1974  Fiore et al. ........................ 203/29

FOREIGN PATENT DOCUMENTS 5-271217  10/1993  Japan .

OTHER PUBLICATIONS

Levenspiel, Octve., "Chemical Reaction Engineering," $2^{nd}$ ed, pp. 144–145, 1972, John Wiley & Sons.

Primary Examiner—Ba K. Trinh
Attorney, Agent, or Firm—James M. Hunter, Jr.

[57] ABSTRACT

A method of preparing cyclic formals which contain only small amounts of by-product impurities and unreacted starting materials, and which are ready to be purified.

In preparing a cyclic formal by reacting alkylene glycol with formaldehyde in the presence of a catalyst, a reaction vessel provided with a vapor-liquid contact zone at the upper part thereof is used. Vapor generated from the reaction mixture and containing a cyclic formal goes up and passes through the vapor-liquid contact zone to be condensed. While part of the condensate is returned to the vapor-liquid contact zone, the remainder of the condensate is taken out as a distillate.

6 Claims, 2 Drawing Sheets

METHOD OF PREPARING CYCLIC FORMALS

BACKGROUND OF THE INVENTION

1. Field of the Invention

The present invention relates to a method of preparing cyclic formals which are useful as solvents, intermediates of drugs, detergents, starting materials for resins, and like substances. More particularly, it relates to a method of preparing cyclic formals which contain only small amounts of by-product impurities or unreacted starting materials.

2. Description of the Related Art

Cyclic formals typified by 1,3-dioxolan, 1,4-butanediol formal, diethylene glycol formal, 4-methyl-1,3-dioxolan, 1,3-dioxan and 1,3,5-trioxepan are known to be obtainable from a cyclizing reaction between a corresponding glycol and an aldehyde, and between a corresponding alkylene oxide and an aldehyde. For example, German patent No. 1914209 discloses a process for preparing a typical cyclic formal, 1,3-dioxolan, by reacting glycol with formaldehyde in the presence of an acid catalyst, and Ind. Eng. Chem., 46,787(1954) and U.S. Pat. No. 3,857,759 both disclose a process for preparing 1,3-dioxolan by reacting glycol and paraformaldehyde in the presence of an acid catalyst.

However, research conducted by the inventors of the present invention on a method of preparing cyclic formals starting from a glycol and an aldehyde revealed that considerable amounts by-product impurities and unreacted starting materials, especially formaldehyde, were contained in the distillate obtained when an ordinary reaction vessel of an evaporator type was used for the reaction and the vapor produced was taken out continuously. The presence of by-product impurities or unreacted starting materials in a distillate should be avoided if possible since it greatly affects the subsequent purification process of cyclic formals and renders the purification process cumbersome and complicated.

SUMMARY OF THE INVENTION

The object of the present invention is to provide a method of preparing a cyclic formal which contains only small amounts of by-product impurities and unreacted starting materials and which is easy to purify.

In order to achieve this object, the inventors of the present invention conducted extensive studies of devices including a reaction vessel, and have found that a prescribed reaction vessel used in a prescribed manner to be described below can significantly reduce the amounts of impurities produced as by-products and unreacted starting materials, leading to completion of the invention.

Accordingly, the present invention provides a method of preparing a cyclic formal by reacting alkylene glycol with formaldehyde in the presence of a catalyst. The starting materials are supplied to a reaction vessel provided with a vapor-liquid contact zone at the upper part of the vessel. Vapor containing a cyclic formal, which is generated from the reaction mixture and which has risen and passed through the vapor-liquid contact zone is allowed to condense. Part of the condensate is refluxed into the vapor-liquid contact zone, and the remainder of the condensate is taken out as a distillate.

In one form of the invention, the vapor-liquid contact zone is a distillation tower.

In a preferred embodiment, the vapor is condensed in an exterior condenser connected to the reaction vessel.

The method of the present invention is particularly suitable for but not limited to preparing 1,3-dioxolan.

The above and other objects, features and advantages of the present invention will become apparent from the following description.

DETAILED DESCRIPTION OF THE INVENTION AND PREFERRED EMBODIMENTS

The species of alkylene glycol which is used in the present invention depends on the cyclic formal to be prepared: Ethylene glycol is used for preparing 1,3-dioxolan, 1,4-butanediol is used for 1,4-butanediol formal, diethylene glycol is used for diethylene glycol formal, 1,2-propane diol is used for 4-methyl-1,3-dioxolan, 1,3-propanediol is used for 1,3-dioxane, and 2-(hydroxymethoxy)ethanol is used for 1,3,5-trioxepan. The method of the present invention is particularly useful in the preparation of 1,3-dioxolan using ethylene glycol.

Generally, the source of formaldehyde, which is another starting material for carrying out the method of the present invention, is an aqueous solution of formaldehyde, formaldehyde gas or paraformaldehyde. Of these, an aqueous solution of formaldehyde is preferred.

The catalyst which is used in the present invention is preferably an acidic catalyst, and examples thereof include mineral acids such as sulfuric acid and phosphoric acid; aliphatic or aromatic sulfonic acids such as hetero polyacid, methanesulfonic acid, benzenesulfonic acid, paratoluenesulfonic acid and naphthalin sulfonic acid; ion-exchange resins; ion-exchange fibers; ion-exchange membranes; zeolite and solid acids such as silica alumina.

The reaction conditions under which alkylene glycol and formaldehyde are reacted in the presence of a catalyst depend on the starting materials and the catalyst to be used, but generally speaking, conventionally known conditions are applicable. Taking the preparation of 1,3-dioxolan as an example, the reaction temperature ranges from 75° to 160° C., preferably from 90° to 140° C., and the average residence time ranges from 1 to 300 minutes, preferably from 5 to 120 minutes. In general, the method according to the present invention is applied to a continuous process, but it can also be applied to a batch system.

Figure 1:
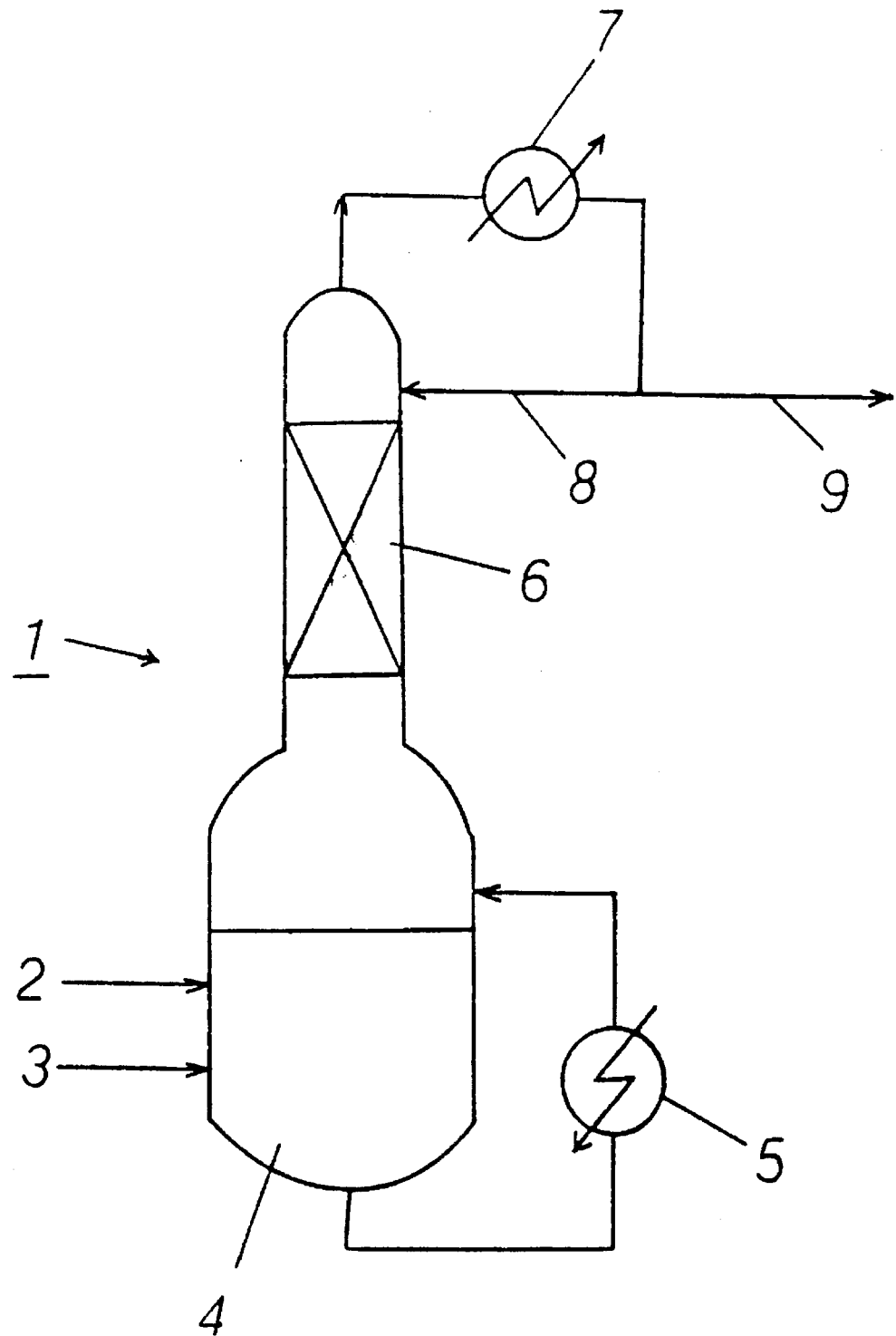
FIG. 1 is a schematic illustration showing an example of a system which can be used for performing the method of preparing cyclic formals according to the present invention.

The present invention will now be described with reference to an example of the distillation system shown in FIG. 1. In FIG. 1, only essential components of the system are shown and nonessential components are omitted for the sake of simplicity. Reference numeral 1 indicates a reaction vessel provided with a vapor-liquid contact zone 6, numeral 2 indicates a supply line of alkylene glycol, numeral 3 indicates a supply line of a source of formaldehyde, numeral 4 indicates a reaction mixture (reaction liquid), numeral 5 indicates a reboiler for heating the reaction mixture, numeral 7 indicates an overhead condenser provided outside the reaction vessel 1, numeral 8 indicates a reflux line of a condensate, and numeral 9 indicates a line for taking out the distillate. The reaction mixture is heated by means such as a reboiler or by any ordinary heaters as long as they can directly heat the bottom of the reaction vessel. If necessary, the reaction vessel is equipped with a line for discharging the reaction mixture. The system of FIG. 1 is an example in which a reaction product is evaporated in the reaction vessel and subjected to vapor-liquid contact. However, the present invention also encompasses the case in which the reaction is performed in another reaction vessel and the reaction mixture is introduced to a system as shown in FIG. 1 to undergo subsequent steps.

In the present invention, the vapor-liquid contact zone 6 is provided in order to force the vapor generated from the reaction mixture and reflux liquid to achieve vapor-liquid contact. This zone is preferably a distillation tower. There is no particular limitation on the type of the distillation tower which can be used, and a plate distillation tower and a packed distillation tower are both suitable. In cases where a plate distillation tower is used, any known types are usable, such as bubble cap trays, uniflux trays, bulb trays, Natter bulb trays, ballast trays, sieve trays, venturi trays, Kittel trays, turbo grid trays, and ripple trays.

If the distillation tower is a packed distillation tower, any type of packing materials is usable including ring types such as Raschig rings, Lessing rings, divided rings and pole rings; saddle types such as bar saddles and interlock saddles; and other types such as Goodroigh packings, Stedman packings, Dickson rings, McMahon packings, helix packings, teralet, and cross-spiral packings.

The number of plates of the above-mentioned vapor-liquid contact zone is 1 or more, and preferably 3 or more. In packed distillation towers, the theoretical number of plates is preferably 0.5 or more, more preferably 1 or more, and most preferably 3 or more. In any event, if the number of plates (or theoretical plates) increases, the effect of the present invention obtained per each increased plate decreases. Therefore, from the viewpoint of cost of installation, it is preferable that the number of plates of plate distillation towers be 20 or less, particularly 10 or less, and the number of theoretical plates of packed distillation towers be 10 or less, particularly 5 or less.

The alkylene glycol and the source of formaldehyde which are supplied to the reaction vessel via the supply lines 2 and 3 are heated with a reboiler 5 and are allowed to react in the presence of a catalyst which is separately supplied, thereby producing a cyclic formal. The reaction mixture contains the cyclic formal produced, water originally contained in starting materials, water produced as a by-product, formaldehyde and alkylene glycol which are the starting materials, and other impurities produced as by-products. The vapor which is generated from the reaction mixture in the reaction vessel contains these substances. In the present invention, however, since a vapor-liquid contact zone 6 is provided at the upper part of the vessel, the ascending vapor contacts the below-described reflux liquid which comes down from the upper part of the vessel, thereby significantly reducing the amounts of the by-product impurities and unreacted starting materials which are contained in the distillate 9. The vapor which contains a cyclic formal and which has passed through the vapor-liquid contact zone 6 is condensed in an overhead condenser 7. Part of the condensate is returned to the upper part of the vapor-liquid contact zone 6 of the reaction vessel 1 via a reflux line 8, and the remainder of the condensate is taken out through a distillate output line 9. The reflux ratio is generally in the range of 0.2 to 5, and preferably 0.5 to 3.

According to the method of the present invention, the cyclic formal taken out from the distillation output line 9 contains only significantly reduced amounts of impurities. The method of the present invention is particularly useful for preparing 1,3-dioxolan.

As described above, the distillate obtained according to the present invention contains a cyclic formal, water, and in addition, unreacted starting materials such as formaldehyde in reduced amounts, and trace amount of impurities produced as by-products. Therefore, in order to prepare a purified cyclic formal, a purifying process such as distillation is required in general. In most cases, purification of cyclic formals beyond a certain purity is difficult due to the phenomenon known as azeotropy between cyclic formals and water. In such a case, azeotropic distillation, extraction distillation, salting out, and similar methods can be employed for effecting a purification.

EXAMPLES

The present invention will further be described in detail by way of examples, which should not be construed as limiting the invention.

Example 1

Figure 2:
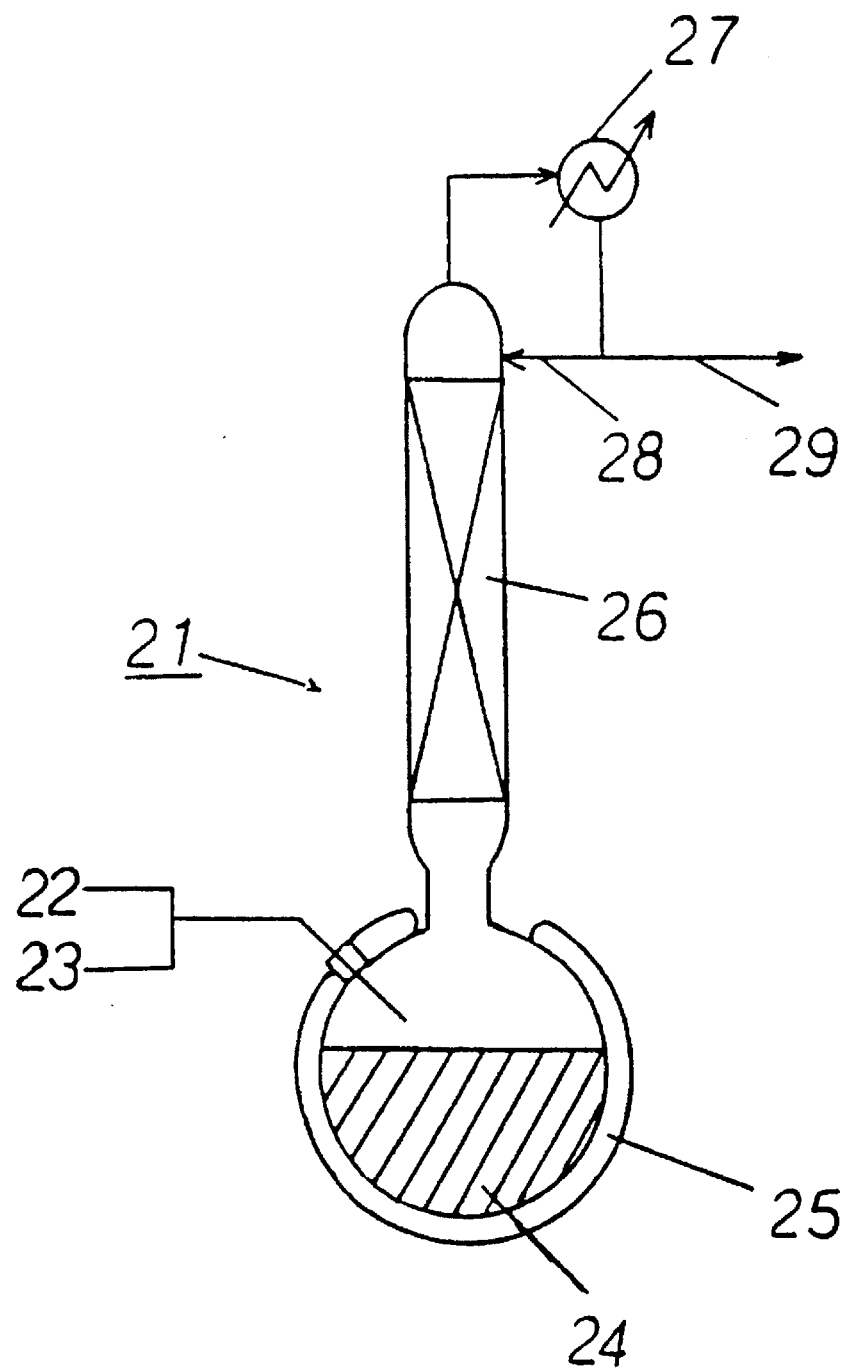
FIG. 2 is a schematic illustration showing the apparatus used in Example 1 of the present invention.

A reaction vessel 21 as shown in FIG. 2 having a round bottom (volume of the round bottom: 2 liters) equipped with a distillation tower 26 (40 mm in diameter, 400 mm high, packed with glass beads) for providing a vapor-liquid contact zone at the upper part of the vessel was used. 540 g of ethylene glycol, 523 g of an aqueous solution of formaldehyde containing 0.7% methanol (concentration of formaldehyde: 50% by weight) and 5 g of sulfuric acid were charged in the reaction vessel and heated (heater 25) at 100° to 120° C. Fractions which boiled between 70° to 100° C. were removed. During the distillation, ethylene glycol (line 22) and the aqueous solution of formaldehyde (line 23) were supplied to the reaction vessel in flow rates of 1:1 on a molar basis, so that the height of the reaction mixture was maintained at a substantially constant level. The reflux ratio (overhead condenser 27, reflux line 28) was 1.0. The composition of the distillate (line of taking out the distillate 29) is shown in Table 1.

TABLE 1

|  | Composition (% by weight) |
| --- | --- |
| 1,3-Dioxolan | 64.9 |
| 1,3,5-Trioxepan | 2.6 |
| Water | 31.6 |
| Formaldehyde | 0.8 |
| Methanol | 0.1 |
| Ethylene glycol | 0.0 |

Comparative Example 1

The procedure of Example 1 was repeated except that the glass beads were eliminated from the distillation tower 26 and the vapor generated from the reaction mixture was permitted to distill off. The composition of the distillate obtained is shown in Table 2. As apparent from the data, contents of formaldehyde and ethylene glycol, which were starting materials, and impurities in the distillate were high.

TABLE 2

|  | Composition (% by weight) |
| --- | --- |
| 1,3-Dioxolan | 62.5 |
| 1,3,5-Trioxepan | 3.8 |
| Water | 30.6 |
| Formaldehyde | 2.5 |
| Methanol | 0.2 |
| Ethylene glycol | 0.4 |

As described above, the present invention provides a method of preparing a cyclic formal which contains only small amounts of impurities in the form of by-products and unreacted starting materials of alkylene glycol and formaldehyde, and which can simplify the subsequent purification process. Accordingly, the present invention is very useful and advantageous in industry.

I claim:

1. A method of preparing a cyclic formal by reacting alkylene glycol with formaldehyde in the presence of a catalyst selected from the group consisting of phosphoric acid, sulfuric acid, methane sulfonic acid, benzene sulfonic acid, paratoluene sulfonic acid, naphthalin sulfonic acid, ion exchange resins, ion exchange fibers, ion exchange membranes, zeolite, and silica alumina, comprising:

(a) supplying alkylene glycol and formaldehyde to a reaction vessel provided with a vapor-liquid contact zone at the upper part of the vessel;

(b) allowing vapor to generate from the reaction mixture, said vapor containing the cyclic formal;

(c) passing the vapor through the vapor-liquid contact zone to form a condensate, said condensate containing the cyclic formal;

(d) refluxing part of the condensate into the vapor-liquid contact zone; and (e) removing the remainder of the condensate from the vapor-liquid contact zone as a distillate, cyclic formal product, wherein the distillation occurs in the absence of ethylene glycol or the formation of formic acid.

2. The method according to claim 1, wherein the vapor-liquid contact zone is a distillation tower.

3. The method according to claim 1, wherein the vapor is condensed in an exterior condenser connected to the reaction vessel.

4. The method according to claim 1, wherein the cyclic formal is 1,3-dioxolan.

5. The method according to claim 2, wherein the cyclic formal is 1,3-dioxolan.

6. The method according to claim 3, wherein the cyclic formal is 1,3-dioxolan.

* * * * *